United States Patent [19]

Chien et al.

[11] 4,053,580

[45] Oct. 11, 1977

[54] MICROSEALED PHARMACEUTICAL DELIVERY DEVICE

[75] Inventors: Yie W. Chien, Skokie; Howard J. Lambert, Deerfield, both of Ill.

[73] Assignee: G. D. Searle & Co., Chicago, Ill.

[21] Appl. No.: 724,688

[22] Filed: Sept. 20, 1976

Related U.S. Application Data

[60] Continuation-in-part of Ser. No. 617,542, Sept. 29, 1975, Pat. No. 3,992,518, which is a division of Ser. No. 517,454, Oct. 24, 1974, Pat. No. 3,946,106.

[30] Foreign Application Priority Data

Oct. 23, 1975 Argentina .............................. 260899

[51] Int. Cl.$^2$ ......................... A61K 9/00; A61K 9/52; A61K 47/00
[52] U.S. Cl. ..................... 424/15; 128/260; 424/14; 424/16; 424/19; 424/22
[58] Field of Search ..................... 128/260; 424/14–22

[56] References Cited

U.S. PATENT DOCUMENTS

| | | | |
|---|---|---|---|
| 3,279,996 | 10/1966 | Long et al. ............................ | 424/19 |
| 3,518,340 | 6/1970 | Raper .................................... | 264/251 |
| 3,545,439 | 12/1970 | Duncan ................................. | 128/260 |
| 3,710,795 | 1/1973 | Higuchi et al. ....................... | 128/260 |
| 3,797,485 | 3/1974 | Urquhart .............................. | 128/213 |
| 3,832,458 | 8/1974 | Merrill ................................... | 424/19 |
| 3,845,761 | 11/1974 | Zaffaroni ............................... | 128/130 |
| 3,946,106 | 3/1976 | Chien et al. .......................... | 424/15 |
| 3,992,518 | 11/1976 | Chien et al. .......................... | 424/22 |

*Primary Examiner*—Shep K. Rose
*Attorney, Agent, or Firm*—John J. McDonnell

[57] ABSTRACT

The present invention is concerned with a pharmaceutical delivery device comprising a biologically acceptable silicone polymer matrix having microsealed compartments of 10–200 microns throughout, wherein the microsealed compartments contain a pharmaceutical in a hydrophilic solvent system. The biologically acceptable silicone polymer matrix is formed by in situ cross linking of a liquid, biologically acceptable silicone polymer in an emulsion of pharmaceutical in the hydrophilic solvent system and liquid biologically acceptable silicone polymer. The biologically acceptable silicone polymer matrix is placed in a sealed or unsealed biologically acceptable polymer container. The rate of release of pharmaceutical is controlled by altering the solubility characteristics of the hydrophilic solvent system and/or the biologically acceptable polymer matrix, the rate of release being independent of the time when the ratio of the partition coefficient of the pharmaceutical between the hydrophilic solvent system and biologically acceptable silicone polymer matrix to the solubility of the pharmaceutical in the hydrophilic solvent system is between 1 and $10^{-4}$ ml/mcg.

26 Claims, No Drawings

MICROSEALED PHARMACEUTICAL DELIVERY DEVICE

This is a continuation-in-part of Ser. No. 617,542, filed Sept. 29, 1975, now U.S. Pat. No. 3,992,578 which is a division of Ser. No. 517,454, filed Oct. 24, 1974, now U.S. Pat. No. 3,946,106.

The present invention is concerned with a pharmaceutical delivery device comprising a biologically acceptable polymer container and an inner biologically acceptable silicone polymer matrix contained within the biologically acceptable polymer container, the inner biologically acceptable silicone polymer matrix having microsealed compartments throughout, the microsealed compartments containing a pharmaceutical in a hydrophilic solvent system, wherein the ratio of the partition coefficient of the pharmaceutical between hydrophilic solvent system and the inner biologically acceptable silicone polymer matrix to the solubility of the pharmaceutical in hydrophilic solvent system is between 1 and $10^{-4}$ ml/mcg, the pharmaceutical being diffusable through the inner biologically acceptable silicone polymer matrix and biologically acceptable polymer container at a therapeutically effective constant rate when the microsealed pharmaceutical delivery device is in an aqueous environment, the hydrophilic solvent system being non-diffusable through the inner biologically acceptable silicone polymer matrix and biologically acceptable polymer container.

Biologically acceptable polymer containers are containers adapted in size and shape for implanting in a body cavity or surgically under or on the skin of an animal in need of prolonged administration of a pharmaceutical. For example, the biologically acceptable polymer containers encompassed in this invention may be adapted to serve as a vaginal or an intrauterine insert; it may be adapted as an opthalimic delivery device for insertion in the narrow confines between the eyeball and the ocular cavity; it may be surgically inserted for parenteral administration, and may be adapted for administration of pharmaceuticals to the gastrointestinal tract. The biologically acceptable polymer container may be sealed or unsealed and in this latter aspect is sharply distinguished from polymer membranes surrounding an inner polymer matrix described in U.S. Pat. No. 3,710,795. For example, the container may be a length of flexible biologically acceptable polymer tubing which is sealed or unsealed and also may have additional perforations in the wall of the tubing such that as much as 40% of the inner biologically acceptable silicone polymer matrix is exposed.

Materials used to form the biologically acceptable polymer container are those capable of forming thin walls or coatings through which pharmaceuticals can pass at a controlled rate. Suitable polymers are biologically and pharmaceutically compatible, non-allergenic, and insoluble in and non-irritating to body fluids or tissues with which the device is contacted. The use of soluble polymers is to be avoided since dissolution or erosion of the device would affect there lease rate of the pharmaceutical release rate, as well as the capability of the device to remain in place for convenience of removal. Exemplary materials for fabricating the biologically acceptable polymer container include polyethylene, polypropylene, ethylene/propylene copolymers, ethylene/ethyl acrylate copolymers, ethylene/vinyl acetate copolymers, silicone rubbers, especially the medical grade polydimethyl siloxanes, neoprene rubber, chlorinated polyethylene, polyvinyl chloride; vinyl chloride copolymers with vinyl acetate, poly methacrylate polymer (hydrogel), vinylidene chloride, ethylene, and propylene; polyethylene terephthalate; butyl rubber; epichlorohydrin rubbers; ethylene/vinyl alcohol copolymer; ethylene/vinyl acetate/ vinyl alcohol terpolymer; ethylene/vinyloxyethanol copolymer; and the like. For best results, the biologically acceptable polymer container should be selected from polymers of the above classes with glass transition temperatures below room temperature. The polymer may, but need not necessarily, have a degree of crystallinity at room temperature.

Polymers especially preferred for fabricating the biologically acceptable polymer containers of this invention have the following formula:

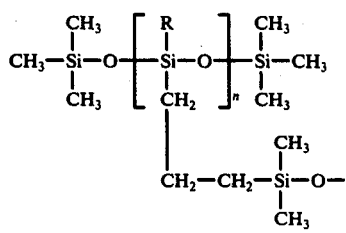

wherein $n$ is about 5000 and R is selected from the group comprising phenyl, lower alkyl, vinyl, or allyl. Suitable polymers for fabricating biologically acceptable polymer containers are described in U.S. Pat. Nos. 3,279,996 and 3,710,795 as well as in *Plastic Materials In Surgery* by Block and Hastings, Charles Thomas, Publisher, Springfield, Ill., 2nd Edition (1972). Desirable polymers are characterized but not limited to the following physical parameters:

|  | Test Value |
|---|---|
| Durometer Hardness(shore A) | 45 to 70 |
| Tensil strength, psi | 1100 |
| Elongation | 500–700% |
| Tear strength lbs/in. | 120–160 |

The inner biologically acceptable silicone polymer matrix is preferably fabricated from room temperature cross-linked silicone rubber (polydimethylsiloxane) such as silicone polymers of the formula:

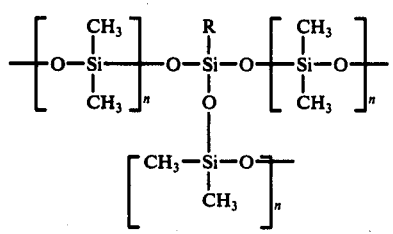

wherein R is alkoxy containing 1–7 carbon atoms, vinyl or allyl and wherein $n$ is about 100–5000.

A saturated solution of pharmaceutical in water and hydrophilic solvent is dispersed throughout liquid silicone polymer by means of high speed stirring before cross-linking of the polymer. The polymer is cross-linked leaving microsealed compartments filled with hydrophilic solvent--water--and pharmaceutical throughout the matrix. The matrix may be constructed in situ in a preshaped biologically acceptable polymer container or the matrix may be preformed and coated with a polymer membrane which serves as a biologically acceptable polymer container. Methods of coating a matrix with biologically acceptable polymers are described in U.S. Pat. No. 3,710,795. Desirable but not exclusive polymers are characterized by the following physical parameters:

| | |
|---|---|
| Durometer Hardness (Shore A) | 45–100 |
| Tensil Strength | 300–1400 |
| Elongation | 100–300% |
| Tear Strength | 20–120 ppi |

The hydrophilic solvent system serves to partition the pharmaceutical between the microsealed compartments and the biologically acceptable silicone polymer matrix. The hydrophilic solvent system must be compatible with the pharmaceutical and must not permeate the polymer or the biologically acceptable silicone polymer container. The hydrophilic solvent system of the present invention comprises water and water miscible solvents which increase the aqueous solubility of te pharmaceutical. Glycols such as polyethylene glycol, propylene glycol, butylene glycol, glycerol formal, and glycofurol are suitable solvents with polyethylene glycol of molecular weight of about 400 being preferred. Amides such as dimethylacetamide and N-($\beta$-hydroxyethyl)-lactamide, ethyl lactate, dioxolanes represent other desirable pharmaceutically compatible water miscible solvents. Ionic and neutral surface active agents in aqueous concentrations above the critical micelle concentration are effective hydrophilic solvent systems. P. H. Elworthy, A. T. Florence, and C. B. Macfarlane, *Solubilization by Surface Active Agents*, Chapman and Hall, 1968 describe the use and selection of surface active agents in pharmaceutical chemistry. Preferred surface active agents are exemplified by sodium dodecyl sulfate, polysorbates, cetyl trimethylammonium bromide, and cetyl-pyridinium chloride.

| | Broad Range % | Preferred Range % |
|---|---|---|
| 1,3-Butanediol | 10–80 v/v | 20–70 v/v |
| Propylene glycol | 10–80 v/v | 20–70 v/v |
| Polyethylene glycol 4000 | 6–96 w/w | 20–70 w/v |
| Polyethylene glycol 6000 | 6–96 w/w | 20–70 w/v |
| Solketal (2,2-dimethyl 1,3-dioxolane-4-methanol) | 5–50 v/v | 20–40 v/v |
| Medical grade dimethyl polysiloxane fluid having a viscosity of 20–12,500 centistokes sold as Medical Fluid 360 by Dow Corning | weight fraction 10–30 w/w % of the polymer matric | |

Solvent systems described above prepared as described for polyethylene glycol 400 provide devices with release rates which are independent of time and releasing 150 – 275 mcg/cm² of ethynodiol diacetate.

Pharmaceuticals permeable through the biologically acceptable inner silicone polymer matrix and biologically acceptable polymer container and meeting the earlier defined solubility requirement may be effectively administered over a long period of time. Scheme I illustrates the required solubility relationship between the pharmaceutical, the hydrophilic solvent system and biologically acceptable silicone polymer matrix.

Scheme I

Crystalline Drug $\xrightarrow{\text{Dissolution Cl}}$ Microsealed liquid Compartment $\xrightarrow{\text{Partition Kb}}$ Polymer phase $\xrightarrow{\text{Permeation}}$ Elution in Solution Solubility of a pharmaceutical (Cl) is measured by constant shaking for 24 hours an excess amount of powdered pharmaceutical in 10 ml. of a hydrophilic solvent system at 37° C. The solution is filtered and the content of the pharmaceutical is measured.

Partition coefficient K(b) is measured by immersing a known surface area of biologically acceptable silicone polymer matrix material in a solution of the pharmaceutical in the hydrophilic solvent system with constant shaking for 24 hours and then measuring the amount of pharmaceutical remaining in the solvent system.

;ti Kb = (Ci − Cl/Ci)

Ci = initial concentration of pharmaceutical
Cl = Equilibrium concentration of pharmaceutical Table I is illustrative of the relation between Cl, Kb, release rate, and kinetics of release of 17$\alpha$-ethynyl-4-estrene-3$\beta$,17$\beta$-diol 3,17-diacetate (ethynodiol diacetate) in a hydrophilic solvent system of polyethylene glycol having a molecular weight of about 400.

Table I

| MICROSEALED LIQUIDS COMPARTMENTS | PHARMACEUTICAL SOLUBILITY (mcg/ml) | PARTITION COEFFICIENT | Kb/Cl (ml/mcg) | Rate of Pharmaceutical Release (gm/10⁶cm²) | Kinetics* |
|---|---|---|---|---|---|
| 100% PEG 400 | 45600 | 0.032 | $7.0 \times 10^{-7}$ | 1095/day$^{\frac{1}{2}}$ | Q - t$^{\frac{1}{2}}$ |
| 80% PEG 400 | 4460 | 0.332 | $7.4 \times 10^{-5}$ | 1203/day$^{\frac{1}{2}}$ | Q - t$^{\frac{1}{2}}$ |
| 60% PEG 400 | 437 | 3.385 | $7.8 \times 10^{-3}$ | 319.4/day | Q - t |
| 50% PEG 400 | 156 | 9.48 | $6.1 \times 10^{-2}$ | 315.6/day | Q - t |
| 30% PEG 400 | 64.6 | 22.9 | 0.355 | 297.8/day | Q - t |

*Q - t$^{1/2}$ relationship (matrix-controlled process) indicates that the amount of pharmaceutical released decreases with time and Q - t relationship (partition controlled process) indicates that a constant amount of pharmaceutical is released independent of time.

A wide variety of pharmaceuticals may be administered over a long period of time. Steroids, alkaloids, fatty acids and lipid soluble vitamins are typical pharmaceutical agents which may be incorporated into the microsealed compartments of the present pharmaceutical delivery device. Representative pharmaceuticals which are advantageously administered by the present delivery device are: Estrogens: Mestranol, ethynyl estradiol, estrone, estradiol, estradiol-3-methyl ether diethylstilbestrol, and related estrogens and ester derivatives thereof described at pages 423–429 in Cutting's *Handbook of Pharmacology*, Appleton-Century-Crofts, New York, 1969.

Progestins: Progesterone, 17α-ethynyl-4-estrene-3β,17β-diol diacetate, 17α-ethynel-11β-methyl-4 estrene 3β, 17β-diol 3,17-diacetate, 17α-acetoxy-11β-methyl-19-norpregn-4-en-3-one, and progestins listed on pages 420 to 436 in Cutting's Handbook of Pharmacology.

Androgens:Testosterone, testosterone propionate, testosterone phenylacetate and related androgens described in Cutting's Handbook of Pharmacology at pages 442 to 448. Adrenal Cortical Hormones: Desoxycorticosterone acetate, prednisolone, and those described at pages 395 to 412 in Cutting's Handbook of Pharmacology.

Diuretics (Mineralcorticoid Blocking agents): 7α-ethoxy=carbonyl-17-hydroxy-3-oxo-17α-pregn-4-ene-21-carboxylic acid γ-lactone, 17-hydroxy-7β-methoxycarbonyl-3-oxo-17γ-pregn-4-ene-21-carboxylic acid γ-lactone and diuretics described at page 241–243 of Cutting's *Handbook of Pharmacology*.

Vitamins: Vitamin E, vitamin K and derivatives thereof.

Anti-Protozoal Agents* Nitroimidazoles such as metronidazole.

Furthermore, simple derivatives of the pharmaceuticals (such as ethers, esters, amides, etc.) whichhave desirable polymer solubility and release characteristics, but which are easily hydrolyzed by body pH, enzymes, etc., can be employed.

The amount of drug incorporated in the drug-delivery device varies depending on the particular drug, the desired therapeutic effect, and the time span for which the device provides therapy. Since a variety of devices in a variety of sizes and shapes are intended to provide dosage regimens for therapy for a variety of maladies, there is no critical upper limit in the amount of drug incorporated in the device. The lower limit, too, will depend on the activity of the drug and the time span of its release from the device. Thus, it is not practical to define a range for the therapeutically effective amount of drug to be incorporated in or released by the device.

Those skilled in the pharmaceutical arts will know how to determine toxic levels of a given pharmaceutical, and the minimum effective dose. With this information a proper dosage form can be prepared by measuring the in vivo rate of elution of a given pharmaceutical by standard analytic tecniques e.g. spectroscopic or radio immunoassay analysis. In vitro diffusion of the pharmaceutical from a delivery device may be determined by the methods of Chien and Lambert, J. Pharm. Sci., 63, 365 (1974) or by methods described in U.S. Pat. No. 3,710,795.

A preferred embodiment of the present invention is a microsealed pharmaceutical delivery device comprising a biologically acceptable polymer container constructed of a molecularly oriented heat shrunk, stretched polymeric membrane having reserve elastic recovery stress, an inner biologically acceptable silicone polymr matrix of cross-linked silicone rubber wherein the biologically acceptable silastic polymer matrix has 10–200 micron microsealed compartments distributed throughout, said microsealed compartment containing a pharmaceutical in a hydrophilic solvent system consisting of water and 20–70% polyethylene glycol, said microsealed compartments being formed by in situ cross-linking of the silicone rubber after it is mixed with the hydrophilic solvent system containing a pharmaceutical, the pharmaceutical being diffusible through the inner biologically acceptable silicone polymer matrix and biologically acceptable polymer container at a therapeutically effective constant rate when the microsealed pharmaceutical delivery device is in an aqueous environment, said hydrophilic solvent being non-diffusible through the biologically acceptable silicone polymer matrix and biologically acceptable polymer container.

A most preferred embodiment of the present invention is a microsealed pharmaceutical delivery device comprising a biologically acceptable polymer container constructed of silicone polymers of the the formula

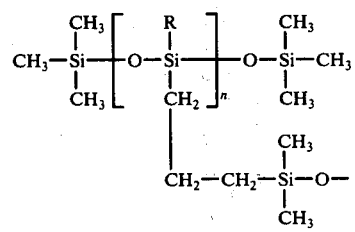

wherein n is about 5000 and R is phenyl, alkyl, vinyl or allyl or polycarbonate copolymers thereof, an inner biologically acceptable silicone polymer matrix constructed of cross-linked silicone polymer of the formula

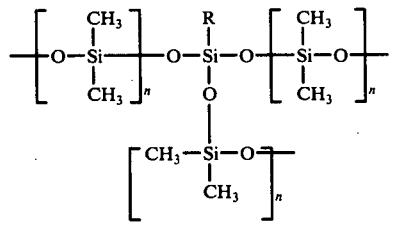

wherein R is alkoxy, alkyl, phenyl, vinyl or allyl and wherein n is about 100 to 5000 and wherein the inner biologically acceptable silicone polymer matrix has microsealed compartments distributed throughout, said microsealed compartments containing a pharmaceutical in a hydrophilic solvent system consisting of water and 20–70% polyethylene glycol, said microsealed compartments being formed by in situ cross-linking of the liquid silicone polymer after it is emulsified with hydrophilic solvent system containing the pharmaceutical, the pharmaceutical being diffusible through the inner biologically acceptable silicone polymer matrix and biologically acceptable polymer container at a therapeutically effective constant rate when the microsealed pharmaceutical delivery device is in an aqueous environment, said hydrophilic solvent being non-diffusible through the inner biologically acceptable silicone polymer matrix and biologically acceptable polymer container.

A biologically acceptable silicone polymer matrix containing a pharmaceutical in a hydrophilic solvent system is prepared as follows: 2 parts of a 40% polyethylene glycol (molecular weight 380–420) in water is saturated with 2 parts of ethynodiol diacetate at 37° C.

by vigorous agitation for 10 minutes. To this mixture is added 6 parts of liquid silicone polymer of the formula

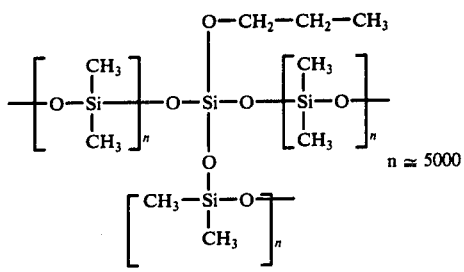

sold as Silastic ® Medical Grade 382 Elastomer by Dow-Corning and this combination is stirred with a mechanical mixer at 1000 rpm for 28 minutes. 0.015 Parts of a cross-linking agent (stannous octanoate is added to the combination and stirring is continued for 2 minutes. The combination is placed in a silicone rubber tubing (I.D. 3.18mm, O.D. 6.35mm sold by Dow-Corning as Medical Grade Silastic Tubing No. 601-365). This tubing is a silicone polymer of the formula

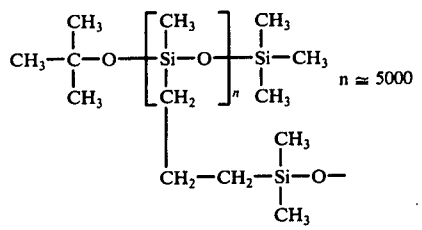

The system is allowed to cross-link for 1 hour and then the tubing is sectioned to provide pharmaceutical delivery devices with the desired amount of pharmaceutical. The ends of the sections may be sealed or left open and additional openings may be made in the walls of the tubing to facilitate higher but still constant rates of release. This device releases 315.6 mcg/cm²/day of ethynodiol diacetate. Replacement of the ethynodiol diacetate with 2 parts of one of the following pharmaceuticals provides the indicated release rate:

|  | Release Rate mcg/cm²/day |
| --- | --- |
| 17α-acetoxy-11β-methyl-19-norpregn-4-ene-3,20-dione | 51.89 |
| Desoxycorticosterone acetate | 55.1 |
| 17-hydroxy-7β-methoxycarbonyl-3-oxo-17α-pregn-4-ene-21-carboxylic acid γ-lactone | 63.08 |
| 7α-acetylthio-17α-(2-carboxyethyl)-17β-hydroxyandrost-4-3n-3-one lactone | 18.25 |
| metronidazole | 4.23 |

The present invention encompasses a method of distributing a pharmaceutical throughout a biologically acceptable silicone polymer comprising (a) emulsifying a mixture of a liquid biologically acceptable silicone polymer and hydrophilic solvent system containing a pharmaceutical and (b) in situ cross-linking of the liquid biologically acceptable silicone polymer to form a biologically acceptable silicone polymer matrix, said biologically acceptable silicone polymer matrix having microsealed compartments of 10 to 200 microns throughout, said microsealed compartments containing the pharmaceutical and the hydrophilic solvent system.

Preferably the present invention encompasses a method of distributing a pharmaceutical throughout a biologically acceptable silicone polymer comprising:

a. emulsifying a mixture of a biologically acceptable liquid silicon polymer of the formula

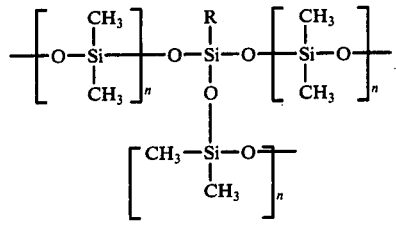

wherein R is alkoxy containing 1-7 carbon atoms, alkyl containing 1-10 carbon atoms, or allyl and n = 100-5000 with a pharmaceutical in a hydrophilic solvent system of 20-70% polyethylene glycol in water; and b. in situ cross linking the biologically acceptable liquid silicone polymer to form a biologically acceptable silicone polymer matrix having microsealed compartments of 10-200 microns throughout, said microsealed compartments containing the pharmaceutical in the hydrophilic solvent system.

Thus, the present invention encompasses an improvement in known pharmaceutical delivery devices, the improvement comprising a biologically acceptable polymer matrix having 10-200 micron microsealed compartments throughout, the microsealed compartments containing a pharmaceutical in a hydrophilic solvent system; the improvement providing for control of the release rate of the pharmaceutical as a function of time.

A number of pharmaceutical delivery devices wherein a pharmaceutical is enclosed in a polymer are known. U.S. Pat. No. 3,279,996 describes an implantate comprising a pharmaceutical delivery device consisting of a pharmaceutical enclosed in silicone polymer. The present device is particularly distinguished in that the pharmaceutical in a hydrophilic solvent system is contained in microsealed compartments distributed throughout the silicone polymer matrix. U.S. Pat. No. 3,279,996 describes in situ polymerization of a liquid silicone polymer containing a pharmaceutical in vivo, but there is no hydrophilic solvent to control the rate of pharmaceutical release or for the formation of microsealed compartments. The presence of microsealed compartments was established by replacing the pharmaceutical with a hydrophilic dye and visually observing with the aid of a microscope the location of the dye in discrete microsealed pockets. It has also been observed that pharmaceuticals which are highly soluble in silicone polymer such as ethynodiol diacetate have a release rate from silicone rubber inplantates porportional to the square root of time ($T^{1/2}$) in the absence of microsealed compartments containing a suitable hydrophilic solvent. A silicone rubber capsule containing crystalline drug within as described in U.S. Pat. No. 3,279,996 likewise has a rate of release proportional to $T^{1/2}$ and has an inherent danger of an overdose resulting from a ruptured capsule. No such danger exists with the present pharmaceutical delivery device.

U.S. Pat. No. 3,710,795 describes a pharmaceutical delivery device comprising an inner polymer matrix with crystalline pharmaceutical distributed throughout and an outer polymer membrane surrounding the inner polymer matrix. The present device is particularly distinct in that the pharmaceutical in a hydrophilic solvent is contained in microsealed compartments throughout the inner polymer matrix. The delivery system described in U.S. Pat. No. 3,710,795 releases pharmaceutical at rates proportional to the square root of time ($T^{1/2}$) where as in the delivery system of the present invention the rate of druge release may be altered from $T^{1/2}$ to $T^0$ (independent of time9 by adjusting the solubility characteristics of the hydrophilic solvent system (Table I). The use of 30–60% polyethylene glycol results in a rate of release independent of time ($T^0$) whereas the use of larger percentages of polyethylene glycol results in a rate of release proportional to $T^{1/2}$. Thus, in the present system the relationship of the rate of release to time may be controlled by selection of an appropriate solvent. It is also noted that the delivery devices of the present invention do not have to be surrounded by an outer membrane. In fact, up to 40% of the inner matrix may be exposed. Exposing the inner matrix advantageously increases the rate of pharmaceutical released without altering the relationship of the release rate to time, i.e. in a constant rate delivery device exposure of the inner matrix results in a higher but constant rate of release.

U.S. Pat. No. 3,545,439 describes pharmaceutical delivery devices prepared by mixing the pharmaceutical with a liquid silicone rubber and then in situ cross-linking the liquid silastic rubber at room temperature. The rate of pharmaceutical release profile from these devices is related to $T^{1/2}$. The present devices are advantageous in that the relationship between rate of release and time may be controlled as mentioned above.

The following examples are set forth to illustrate the present invention and are not intended to limit the invention in spirit or in scope. In the following examples parts are given in parts by weight and temperature is in degrees centigrade unless otherwise stated.

EXAMPLE 1

2 Parts of a 40% polyethylene glycol (molecular weight 380–420) in water is saturated with 2 parts of ethynodiol diacetate at 37° C. by vigorous agitation for 10 minutes. To this mixture is added 6 parts of silicone polymer of the formula

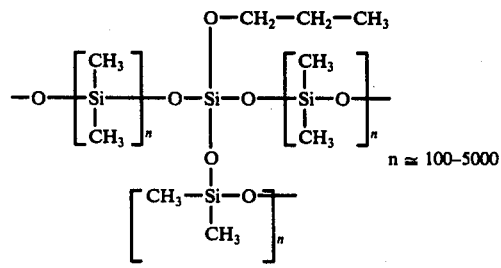

sold as Silastic ® Medical Grade 382 Elastomer by Dow-Corning and this combination is stirred with a mechanical mixer at 1000 rpm for 28 minutes. 0.015 Parts of a cross-linking agent (stannous octanoate is added to the combination and stirring is continued for 2 minutes. The combination is placed in silicone polymer tubing (I.D. 3.18 mm, O.D. 6.35 mm sold by Dow-Corning as Medical Grade Silastic ® tubing No. 601-365). This tubing is a silicone polymer of the formula

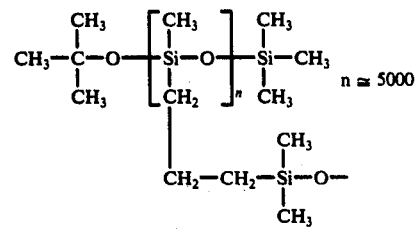

The system is allowed to set for 1 hour and the tubing is sectioned to provide pharmaceutical delivery devices with the desired amount of pharmaceutical.

EXAMPLE 2

The silastic tubing is removed from the biologically acceptable inner polymer matrix and a molecularly bi-axially oriented, heat shrinkable polyethylene film, of 2 mil thickness is embossed about the inner matrix by using conventional metal stamping practice. The silicone polymer matrix is then sandwiched between two pieces of the heat shrinkable polyethylene in the embossed sections so that the matrix is completely enveloped by the film. The film is then heat sealed and cut around the periphery of the matrix. The enshrouded matrix is then heated for 3 seconds at 300° F. resulting in shrinkage of the film and effecting a tight and intimate contact of the film with the pharmaceutical containing silicone polymer matrix.

The heat shrunk polyethylene film may be partially removed to expose the inner polyme matrix to provide a somewhat higher but constant rate of release.

EXAMPLE 3

An emulsion of 2 parts of a 40% polyethylene glycol (molecular weight 380–420) in water is saturated with 2 parts of a 17α-acetoxy-11β-methyl-19-norpregn-4-ene-3,20-dione at 37° C. by vigorous agitation for 10 minutes. To this mixture is added 6 parts of room temperature vulcanizing silicone polymer sold as Silastic ® Medical Grade 382 elastomer by Dow-Corning and this combination is stirred with a mechanical mixer at 1000 rpm for 28 minutes. 0.015 Parts of a cross-linking agent (stannous octoate) is added to the combination and stirring is continued for 2 minutes. The resulting emulsion is placed into heat shrinkable tubing composed of a copolymer of ethylene and vinyl acetate of 82 percent ethylene and 18 percent vinyl acetate. The tubing is of the type rendered heat shrinkable by intermolecular cross-linking followed by molecular orientation as described earlier. The ends of the tubing may be sealed by heat sealing or by the insertion of plugs. The tubing is heat shruk by exposure to air heated at 280° F. for 5–15 seconds. The tubing may be cut into sections and the ends sealed or left unsealed.

EXAMPLE 4

Following the procedure set out in Example 2, a biologically acceptable silastic polymer matrix containing 2 parts of progesterone in place of ethynodiol diacetate is enclosed with heat shrinkable rubber hydrochloride film 1 mil thick by enclosing pre-set the biologically acceptable silicone polymer matrix with molecularly orientated heat shrunk rubber hydrochloride film and heat shrinking at 300° F. for 5 seconds.

EXAMPLE 5

Following the procedure in Example 1, a device containing 17α-acetoxy-11β-methyl-19-norpregn-4-ene-3,20-dione is prepared by using 2 parts of that compound in place of ethynodiol diacetate. This device releases 17α-acetoxy-11β-methyl-19-norpregn-4-ene-3,20-dione at a rate of 51.89 mcg/cm²/day.

EXAMPLE 6

Following the procedure in Example 1, a device containing desoxycorticosterone acetate is prepared by using 2 parts of that compound in place of ethynodiol diacetate. This device releases desoxycorticosterone acetate at a rate of 55.1 mcg/cm²/day.

EXAMPLE 7

Following the procedure in Example 1, a device containing 17-hydroxy-7α-methoxycarbonyl-3-oxo-17α-pregn-4-ene-21-carboxylic acid γ-lactone is prepared by using 2 parts of that compound in place of ethynodiol diacetate. This device releases 17-hydroxy-7β-methoxycarbonyl-3-oxo-17α-pregn-4-ene-21-carboxylic acid γ-lactone at a rate of 63.08 mcg/cm²/day.

EXAMPLE 8

Following the procedure in Example 1, a device containing 7α-acetythio-17α-(2-carboxyethyl) 17β-hydroxyandrost-4-en-3-one lactone is prepared by using 2 parts of that compound in place of ethynodiol diacetate. This device releases 7α-acetylthio-17α-(2-carboxyethyl)-17β-hydroxyandrost-4-en-3-one lactone at a rate of 18.25 mcg/cm²/day.

EXAMPLE 9

Following the procedure in Example 1, a pharmaceutical delivery device is prepared from 6 parts of liquid silicone polymer sold under the trade name of Silastic Medical Grade MDX-4 4210 by Dow-Corning and 1.9 part of ethynodiol diacetate and 0.1 part of mestranol in 2 part 40% polyethylene glycol (molecular weight 400) in water.

What is claimed is:

1. A microsealed pharmaceutical delivery device comprising a sectioned length of flexible medical grade silicone polymer hollow tubing as a biologically acceptable polymer container with as many perforations in the wall of the tubing when unsealed at each end as to expose up to 40% of an inner biologically acceptable silicone polymer matrix contained with the biologically acceptable polymer container, said biologically acceptable silicone polymer matrix having the formula

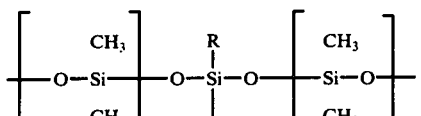

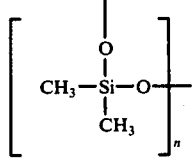

wherein R is alkoxy having 1-7 carbon atoms, alkyl having 1-10 carbon atoms, phenyl, vinyl, or allyl, wherein n is about 100-5000 and having 10-200 micron microsealed compartments throughout, said microsealed compartments containing pharmaceutical saturated 20-70 w/v% polyethylene glycol molecular weight 450-6000, 20-70 v/v% propylene glycol, or 20-70% 1-3-butanediol in water as hydrophilic solvent system.

2. As in claim 1, a microsealed pharmaceutical delivery device comprising a section length of flexible medical grade silicone polymer hollow tubing as a biologically acceptable polymer container with as many perforations in the wall of the tubing when unsealed at each end as to expose up to 40% of an inner biologically acceptable silicone polymer matrix contained and allowed to set within the biologically acceptable polymer container by placing therein a well stirred emulsion of pharmaceutical saturated 20-70 2/v% polyethylene glycol molecular weight 450-6000, 20-70 v/v% propylene glycol, or 20-70% 1-3-butanediol in water as hydrophilic solvent system, medical grade room temperature vulcanizing silicone polymer elastomer and stannous octanoate cross-linking agent; said inner biologically acceptable silicone polymer matrix having 10-200micron microsealed compartments throughout, said microsealed compartments containing a pharmaceutical saturated in said hydrophilic solvent system wherein the ratio of the partition coefficient of the pharmaceutical between the hydrophilic solvent system and inner biologically acceptable silicone polymer matrix to the solutility of the pharmaceutical in the hydrophilic solvent system is between 1 and $10^{-4}$ (ml/mcg), said pharmaceutical being diffusible through the inner biologically acceptable polymer container at a constant rate when the microsealed pharmaceutical delivery deivce is in an aqueous environment, said hydrophilic solvent being non-diffusible through the inner biologically acceptable silicone polymer matrix and biologically acceptable polymer container.

3. As in claim 1 a microsealed pharmaceutical delivery device comprising a biologically acceptable polymer container constructed of flexible medical grade silicone polymer hollow tubing having the formula

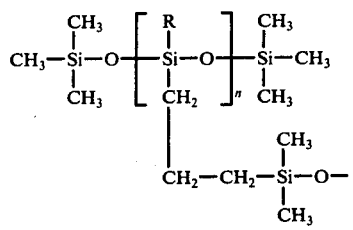

wherein n is about 5000 and R is phenyl, lowerlakyl, vinyl, or allyl and an inner biologically acceptable silicone polymer matrix contained within the biologically acceptable polymer container, said inner biologically acceptable polymer matrix having the formula

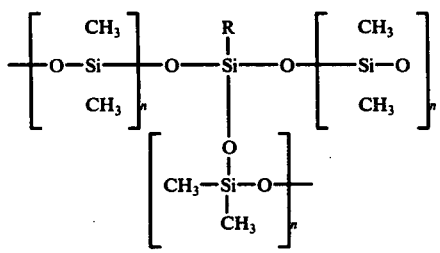

wherein R is alkoxy having 1-7 carbon atoms, alkyl having 1-10 carbon atoms, phenyl, vinyl, or allyl and wherein $n$ is about 100–5000.

4. As in claim 1, a microsealed pharmaceutical delivery device wherein the pharmaceutical is a progestin.

5. As in claim 1, a microsealed pharmaceutical delivery device wherein the pharmaceutical is progesterone.

6. As in claim 1, a microsealed pharmaceutical delivery device wherein the pharmaceutical is 17α-ethynyl-4-estrene-3β,17β-diol diacetate.

7. As in claim 1, a microsealed pharmaceutical delivery device wherein the pharmaceutical is 17α-ethynl-11β-methylestr-4-ene-3β,17β-diol 3,17-diacetate.

8. As in claim 1, a microsealed pharmaceutical delivery device wherein the pharmaceutical is 17α-acetoxy-11β-methyl-19-norpregn-4-en-3,20-dione.

9. As in claim 1, a microsealed pharmaceutical delivery device wherein the pharmaceutical is an estrogen.

10. As in claim 1, a microsealed pharmaceutical delivery device wherein the pharmaceutical is mestranol.

11. As in claim 1, a microsealed pharmaceutical delivery device wherein the pharmaceutical is ethynyl estradiol.

12. As in claim 1, a microsealed pharmaceutical delivery device wherein the pharmaceutical is estradiol-3-methylether.

13. As in claim 1, a microsealed pharmaceutical delivery device wherein the pharmaceutical is estradiol.

14. As in claim 1, a microsealed pharmaceutical delivery device wherein the pharmaceutical is an adrenocortical steroid.

15. As in claim 1, a pharmaceutical delivery device wherein the pharmaceutical is desoxycorticosterone acetate.

16. As in claim 1, a pharmaceutical delivery device wherein the pharmaceutical is prednisolone.

17. As in claim 1, a pharmaceutical delivery device wherein the pharmaceutical is a diuretic.

18. As in claim 1, a pharmaceutical delivery device wherein the pharmaceutical is 7α-ethoxycarbonyl-17-hydroxy-3-oxo-17α-pregn-4-ene-21-carboxylic acid γ-lactone.

19. As in claim 1, a pharmaceutical delivery device wherein the pharmaceutical is 17-hydroxy-;b 7α-methoxycarbonyl-3-oxo-17α-pregn-4-ene-21-carboxylic acid γ-lactone.

20. As in claim 1, a pharmaceutical delivery device wherein the pharmaceutical is diisopropylamino-2-phenyl-2-(pyridyl)butyramide.

21. As in claim 1, a pharmaceutical delivery device wherein the pharmaceutical is testosterone and propionate.

22. As in claim 1, a pharmaceutical delivery device wherein the pharmaceutical is metronidazole.

23. As in claim 1, a pharmaceutical delivery device wherein the pharmaceutical is 7α-acetylthio-17α-(2-carboxyethyl)-17α-hydroxyandrost-4-ene-3-one lactone.

24. As in claim 1, a pharmaceutical delivery device wherein the pharmaceutical is a combination of ethynodiol diacetate and mestranol or ethynylestradiol.

25. As in claim 1, a microsealed pharmaceutical delivery device comprising an unsealed sectioned length of said flexible medical grade silicone polymer tubing as a biologically acceptable polymer container with said inner biologically acceptable silicone polymer matrix contained and set in situ within the biologically acceptable polymer container.

26. As in claim 1, a pharmaceutical delivery device wherein the solvent is 20–60 w/v polyethyleneglycol of molecular weight of about 4000–6000.

* * * * *